US011111518B2

(12) United States Patent
Orenga et al.

(10) Patent No.: US 11,111,518 B2
(45) Date of Patent: *Sep. 7, 2021

(54) MEDIUM FOR THE SPECIFIC DETECTION OF RESISTANT MICROORGANISMS

(71) Applicant: BIOMERIEUX, Marcy l'Etoile (FR)

(72) Inventors: Sylvain Orenga, Neuville-sur-Ain (FR); Céline Roger-Dalbert, Vaux-en-Bugey (FR); John Perry, Newcastle-Upon-Tyne (GB); Vanessa Chanteperdrix, Grenoble (FR); Gilles Zambardi, Trept (FR); Nathalie Bal, Villeurbanne (FR)

(73) Assignee: BIOMERIEUX, Marcy l'Etoile (FR)

(*) Notice: Subject to any disclaimer, the term of this patent is extended or adjusted under 35 U.S.C. 154(b) by 0 days.

This patent is subject to a terminal disclaimer.

(21) Appl. No.: 16/678,502

(22) Filed: Nov. 8, 2019

(65) Prior Publication Data

US 2020/0071742 A1 Mar. 5, 2020

Related U.S. Application Data

(60) Continuation of application No. 15/330,777, filed on Nov. 7, 2016, now Pat. No. 10,494,658, which is a continuation of application No. 14/715,222, filed on May 18, 2015, now abandoned, which is a continuation of application No. 13/539,083, filed on Jun. 29, 2012, now abandoned, which is a division of application No. 11/794,907, filed as application No. PCT/FR2006/050109 on Feb. 9, 2006, now abandoned.

(30) Foreign Application Priority Data

Feb. 10, 2005 (FR) ..................... 05.50394
Oct. 7, 2005 (FR) ..................... 05.53049

(51) Int. Cl.
*C12Q 1/04* (2006.01)
*C12Q 1/10* (2006.01)
*C12Q 1/34* (2006.01)
*C12Q 1/14* (2006.01)
*C12Q 1/37* (2006.01)
*C12Q 1/527* (2006.01)

(52) U.S. Cl.
CPC .............. *C12Q 1/34* (2013.01); *C12Q 1/04* (2013.01); *C12Q 1/045* (2013.01); *C12Q 1/10* (2013.01); *C12Q 1/14* (2013.01); *C12Q 1/37* (2013.01); *C12Q 1/527* (2013.01)

(58) Field of Classification Search
None
See application file for complete search history.

(56) References Cited

U.S. PATENT DOCUMENTS

| | | | |
|---|---|---|---|
| 3,830,700 A | 8/1974 | O'Callaghan et al. | |
| 5,210,022 A | 5/1993 | Roth et al. | |
| 5,358,854 A | 10/1994 | Ferguson | |
| 5,449,612 A | 9/1995 | Lepargneur et al. | |
| 5,510,243 A | 4/1996 | Boyd et al. | |
| 5,534,415 A | 7/1996 | Drenga | |
| 5,610,029 A | 3/1997 | Ehrenfeld et al. | |
| 5,643,743 A | 7/1997 | Chang et al. | |
| 5,962,251 A | 10/1999 | Rambach | |
| 6,350,588 B1 | 2/2002 | Roth et al. | |
| 6,355,449 B1 | 3/2002 | Chen et al. | |
| 6,905,848 B2 | 6/2005 | Hanson et al. | |
| 6,921,635 B1 | 7/2005 | Orenga | |
| 7,052,863 B2 | 5/2006 | Armstrong et al. | |
| 7,148,033 B2 | 12/2006 | Brenner et al. | |
| 7,632,657 B2 | 12/2009 | Rambach et al. | |
| 7,807,439 B2 | 10/2010 | Cotte et al. | |
| 10,494,658 B2 * | 12/2019 | Orenga | C12Q 1/37 |
| 2003/0082667 A1 | 5/2003 | Armstrong et al. | |
| 2004/0121404 A1 | 6/2004 | Cotte et al. | |
| 2005/0009132 A1 | 1/2005 | Rambach | |
| 2005/0112718 A1 | 5/2005 | Nakano et al. | |

FOREIGN PATENT DOCUMENTS

| | | | |
|---|---|---|---|
| AU | 20050112718 B2 | 5/2001 | |
| AU | 773596 B2 | 5/2004 | |
| EP | 0 059 645 A1 | 9/1982 | |
| EP | 0 954 560 B1 | 10/2002 | |
| EP | 1 325 923 A1 | 7/2003 | |
| EP | 1 557 473 A1 | 7/2005 | |

(Continued)

OTHER PUBLICATIONS

Chang et al. "Infection with Vancomycin-Resistant *Staphylococcus aureus* Containing the vanA Resistance Gene". New England Journal of Medicine, vol. 348, No. 14, pp. 1342-1347, 2003.

Kacica et al. "Brief Report: Vancomycin-Resistant *Staphylococcus aureus*—New York, 2004". MMWR Weekly, vol. 53, No. 15, pp. 322-323, 2004.

Whittenbury, R. "The Differentiation of *Streptococcus faecalis* and *S. faecium*". J. Gen. Microbiology, vol. 38, pp. 279-287, 1965.

Chen et al. "Evaluation of D-Xylose and 1% Methyl-α-D-Glucopyranoside Fermentation Tests for Distinguishing Enterococcus gallinarum from Enterococcus faecium". Journal of Clinical Microbiology, vol. 38, No. 10, pp. 3652-3655, 2000.

(Continued)

*Primary Examiner* — Vera Afremova
(74) *Attorney, Agent, or Firm* — Oliff PLC

(57) ABSTRACT

A method for distinguishing among a first group of microorganisms belonging to a first taxon of Gram negative bacteria, the first group of bacteria exhibiting a mechanism of resistance to a treatment; a second group of microorganisms belonging to a second taxon of Gram negative bacteria, the second taxon of bacteria being different than said first taxon, and exhibiting a mechanism of resistance to a treatment identical to the mechanism of the first group; and a third group of Gram negative bacteria that is not resistant to the treatment.

7 Claims, No Drawings

(56) References Cited

FOREIGN PATENT DOCUMENTS

| EP | 1 390 524 B1 | 10/2006 |
|---|---|---|
| FR | 2 728 587 A1 | 6/1996 |
| FR | 2 826 019 A1 | 12/2002 |
| JP | 2000-316597 A | 11/2000 |
| JP | 2004-524041 A | 8/2004 |
| WO | 92/12257 A1 | 7/1992 |
| WO | 92/19763 A1 | 11/1992 |
| WO | 95/04157 A1 | 2/1995 |
| WO | 96/15435 A2 | 5/1996 |
| WO | 98/04674 A1 | 2/1998 |
| WO | 99/09207 A1 | 2/1999 |
| WO | 02/24707 A1 | 3/2002 |
| WO | 02/079486 A2 | 10/2002 |
| WO | 2004/027086 A1 | 4/2004 |
| WO | 2004/040008 A1 | 5/2004 |
| WO | 2004/058995 A1 | 7/2004 |
| WO | 2004-063391 A1 | 7/2004 |

OTHER PUBLICATIONS

Carvalho et al. "Use of Tests for Acidification of Methyl-α-D-Glucopyranoside and Susceptibility to Efrotomycin for Differentiation of Strains of Enterococcus and Some Related Genera". Journal of Clinical Microbiology, vol. 36, No. 6, pp. 1584-1587, 1998.
ChromID by bioMerieux, chromID(TM) VRE Agar, REF 43 004, 15186 B—en—Jul. 2010, Jul. 2010.
Gupta et al. "Antimicrobial susceptibility pattern of vancomycin resistant enterococci to newer antimicrobial agents". Indian Journal of Medical Research, vol. 141, No. 4, pp. 483-486, 2015.
BD BBL Crystal(TM) Identification Systems Gram-Positive ID Kit, Apr. 2004.
FDA Market Approval of the BD BBL Crystal(TM) Identification System, Apr. 2, 1997.
FDA-S Summary on the safety and effectiveness of the BD BBL Crystal (TM) Identification System, May 17, 1996.
Oh et al. "Fluorogenic Selective and Differential Medium for Isolation of Enterobacter sakazakii". Applied and Environmental Microbiology, vol. 70, No. 9, pp. 5692-5694, 2004.
Iversen et al. "A selective differential medium for Enterobacter sakazakii, a preliminary study". International Journal of Food Microbiology, vol. 96, pp. 133-139, 2004.
Manual Codebook of the BD BBL Crystal(TM) Identification Systems, Jul. 1996.
BD BBL Crystal(TM) Identification Systems Gram-Positive ID Kit, Aug. 1999.
Restaino et al. "A Chromogenic Plating Medium for the Isolation and Identification of Enterobacter sakazakii from Foods, Food Ingredients, and Environmental Sources". Journal of Food Protection, vol. 69, No. 2, pp. 315-322, 2006.
BBL Crystal(TM) Identification Systems Gram-Positive ID Kit; 17 pages; 2002; Becton, Dickinson and Company.
Kee et al., "To Proliferate or to Die: Role of id3in Cell Cycle Progression and Survival of Neural Crest Progenitors," 744-755; 2005; Genes and Development.
Mustafa et al., "Inhibition of Bacterial a-glucosidases by Castanosperminein Pure Cultures and Activated Sludge," 68-71; 2002; Applied Microbiology and Biotechnology.
Hanson et al., "Comparison of Simple and Rapid Methods for Identifying Enterococci Intrinsically Resistant to Vancomycin," Journal of Clinical Microbiology, vol. 37, No. 3, pp. 815-817, Mar. 1999.
Boschman et al., "Thirteen-Year Evolution of Azole Resistance in Yeast Isolates and Prevalence of Resistant Strains carried by Cancer Patients at a Large Medical Center," Antimicrobial Agents and Chemotherapy, vol. 42, No. 4, pp. 734-738, Apr. 1998.
Pfaller et al., "Application of CHROMagar Candida for Rapid Screening of Clinical Specimens for Candida albicans, Candida tropicalis, Candida krusei, and Candida (Torulopsis) glabrata," Journal of Clinical Microbiology, vol. 34, No. 1, pp. 58-61, Jan. 1996.

Jarlier V., "Mecanismes de resistances aux antibiotiques," 1997, Medecine Therapeutique, vol. 3, pp. 46-58.
Jacoby G. et al., "Detection of Extended-Spectrum b-Lactamases in Clinical Isolates of Klebsiella pneumoniae and *Escherichia coli*," Apr. 1996, Journal of Clinical Microbiology, vol. 34, No. 4, pp. 908-911.
Cagatay A. et al., "Dio-Sensimedia: A Novel Culture Medium for Rapid Detection of Extended Spectrum b-lactamases," 2003, BMC Infectious Diseases, vol. 3, pp. 1-6.
Navon-Venezia S., Protocol for the Accelerated Detection of Extended-Spectrum b-Lactamase-Producing *Escherichia coli* and Klebsiella pneumoniae Strains from Blood Cultures, Feb. 2004, Eur J Clin Microbiol Infect Dis, vol. 23, pp. 200-202.
Mazoyer M. et al., "Evaluation of CPS ID2 Medium for Detection of Urinary Tract Bacterial Isolates in Speciments from a Rehabilitation Center," Apr. 1995, Journal of Clinical Microbiology, vol. 33, No. 4, pp. 1025-1027.
Davies J. et al., "An Evaluation of MRSA ID: A New Chromogenic Medium for the Isolation and Identification of Methicillin-Resistant *Staphylococcus aureus*," 2004, 14th European Congress of Clinical Microbiology and Infectious Diseases. Prague/Czech Republic.
Perry J. et al., "Development and Evaluation of a Chromogenic Agar Medium for Methicillin-Resistant *Staphyloccus aureus*," Oct. 2004, Journal of Clinical Microbiology, vol. 42, No. 10, pp. 4519-4523.
Ho. P. et al., "Comparison of a Novel, Inhibitor-Potentiated Disc-Diffusion Test with Other Methods for the Detection of Extended Spectrum b-Lactamases in *Escherichia coli* and Klebsiella Pneymoniae," 1998, Journal of Antimicrobial Chemotherapy, vol. 42, pp. 49-54.
Poirel et al. "In vivo-acquisition of high level resistance to imipenem in *Escherichia coli*". Journal of Clinical Microbiology. Aug. 2004, vol. 42, No. 8, pp. 3831-3833.
Martino, M.D.V. et al."The Use of Chromogenic Agar in the Detection of VRE in Stools Samples." American Society for Microbiology, or Microbiology, vol. 103, p. 180, 2003.
Merlino, J. et al. "Evaluation of CHROMagar Orientation for Differentiation and Presumptive Identification of Gram-Negative Bacilli and *Enterococcus* Species." Journal of Clinical Microbiology, vol. 34, No. 7, pp. 1788, 1996.
Devriese, Luc A. et al. "Acidification of Methyl-a-D-Glucopyranoside: a Useful Test to Differentiate Enterococcus casselifiavus and Enterococcus gallinarum from *Enterococcus faecium* Species Group and from Enterococcus faecalis". Journal of Clinical Microbiology, vol. 34, No. 10, pp. 2607-2608, 1996.
Martin, C. et al. "Interet Des Milieux Contenant Des Substrats Chromogenes Pour L'identification et La Numeration Des Bacteries Urinaires". l'Expension Scientifique Francaise, vol. 43, No. 9, pp. 749-753, 1995.
Merlino, J. et al. "Enzymatic Chromogenic Identification and Differentiation of Enterococci". Australian Journal of Medical Science, vol. 19, No. 3, pp. 76-81, 1998.
Facklam, R. "What Happened to the Streptococci: Overview of Taxonomic and Nomenclature Changes". Clinical Microbiology Reviews, vol. 15, No. 4, pp. 613-630, 2002.
Patterson, Thomas S. et al "Simple Method for Detecting Fluconazole-Resistant Yeasts with Chromogenic Agar". Journal of Clinical Microbiology, vol. 34, No. 7, pp. 1794-1797, 1996.
Bradford, Patricia A. "Extended-Spectrum ?-Lactamases in the 21st Century: Characterization, Epidemiology, and Detection of This Important Resistance Threat". Clinical Microbiology Reviews, vol. 14, No. 4, pp. 933-951, 2001.
Oct. 12, 2006 Written Opinion of the International Searching Authority issued in International Application No. PCT/FR2006/050109.
Jul. 13, 2012 Search Report issued in European Patent Application No. EP 11 18 9038.
"GELOSE BLSE: Isolement Selectif Des Enterobacteries Productrices de BLSE". AES Laboratoire, 1999.
Weinbren, M. J. et al., "Rapid Detection of Extended-Spectrum b-Lactamase (ESBL)-Producing Organisms in Blood Culture", Journal of Antimicrobial Chemotherapy, 2005, vol. 55, pp. 131-132.

* cited by examiner

MEDIUM FOR THE SPECIFIC DETECTION OF RESISTANT MICROORGANISMS

CROSS-REFERENCE TO PRIOR APPLICATIONS

This is a continuation of application Ser. No. 15/330,777 filed Nov. 7, 2016, which is a continuation of application Ser. No. 14/715,222 filed May 18, 2015, which is a continuation of application Ser. No. 13/539,083 filed Jun. 29, 2012, which is a divisional of application Ser. No. 11/794,907 filed Jul. 9, 2007, which is a National Stage Application of PCT/FR2006/050109 filed Feb. 9, 2006, and claims the benefit of French Application Nos. 05.50394 filed Feb. 10, 2005 and 05.53049 filed Oct. 7, 2005. The entire disclosures of the prior applications are hereby incorporated by reference herein in their entirety.

The field of the invention is that of microbiological analysis by means of biochemistry, and in particular the detection and identification of microorganisms, for instance of bacteria or yeasts.

Bacterial resistance to antibiotics is a major public health problem. The resistance of infectious microorganisms to a treatment has developed at the same time as anti-infectious molecules and today represents a major obstacle in therapeutics. This resistance is responsible for many problems, including difficulties in detection in the laboratory, limited treatment options and a deleterious impact on clinical outcome.

In particular, the rapid and irrepressible increase in the resistance of pathogenic bacteria, over the last 20 years, represents one of the major current problems in medicine. Infections caused by these organisms are responsible for extended periods of hospitalization and are associated with high morbidity and mortality rates, following therapeutic failures.

Several resistance mechanisms can be involved simultaneously in a bacterial strain. They are generally classified in 3 categories: deficient penetration of the antibiotic into the bacterium, inactivation or excretion of the antibiotic by bacterial enzymatic systems, and lack of affinity between the bacterial target and the antibiotic.

Enzymatic inactivation is the most common mechanism of acquired resistance in terms of number of species and of antibiotics involved. Thus, chromosomal class C cephalosporinases today constitute one of the predominant resistance mechanisms of gram-negative bacteria, the bacteria expressing such enzymes being resistant to cephalosporins. Similarly, β-lactamases are enzymes expressed by certain bacteria, capable of hydrolyzing the C—N bond of the β-lactame ring, the basic structure of antibiotics of the β-lactamine family, so as to give a microbiologically inactive product. Several β-lactamase inhibitors (BLIs), such as clavulanic acid (CA), tazobactam and sulbactam, have been developed in order to increase the antimicrobial activity and broaden the spectrum of the β-lactamines which are associated therewith. They act as a suicide subject for β-lactamases, and prevent enzymatic degradation of the antibiotics and allow them to become effective against bacteria that were initially resistant. However, by virtue of the persistent exposure of strains to antibiotic pressure, the bacteria express their ability to adapt through the continuous and dynamic production of β-lactamases, which evolves at the same time as the development of new molecules.

Gram-negative bacteria which produce high-level chromosome class C cephalosporinases (reference is made to HL Case bacteria), and also gram-negative bacteria which produce extended-spectrum β-lactamase (reference is then made to ESBL bacteria) have, as a result, become an increasing threat, in particular because the number of bacterial species concerned is increasing. HL Case and ESBL bacteria are resistant to treatments based on 1st- and 2nd-generation penicillins and cephalosporines, but also on 3rd-generation cephalosporines (C3G) (cefotaxim CTX, ceftazidime CAZ, cefpodoxime CPD, ceftriaxone CRO) and monobactams (aztreonam ATM). On the other hand, 7α-methoxycephalosporins (cephamycins: cefoxitin, cefotetan) and carbapenems (imipenem, meropenem, ertapenem) generally conserve their activity. ESBLs are inhibited by β-lactamase inhibitors (BLIs), which makes it possible to differentiate them from other cephalosporinases.

These bacteria thus most commonly simultaneously express resistances to several treatments, which poses difficulties in setting up a relevant treatment and avoiding therapeutic failures. An *Escherichia coli* bacterium can thus be HL Case and ESBL. In addition, since ESBL-positive enterobacteria have a tendency to disseminate the resistance by clonal transmission of strains or conjugative plasma transfer, they represent a problem in terms of controlling infections. In most studies, *Escherichia coli* and *Klebsiella pneumoniae* remain the most common ESBL-producing species. However, over the last few years, ESBLs have greatly broadened their panel of host species. In fact, many species of enterobacteria and of nonfermenting gram-negative bacilli (such as *Pseudomonas aeruginosa*) have also been reported to ESBL producers.

In addition to these ESBL bacteria, mention may also be made of *Staphylococcus aureus* bacteria, which are also pathogenic bacteria that develop many mechanisms of resistance, such as resistance to methicillin, penicillin, tetracycline, erythromycin, or vancomycin. *Enterococcus faecium* is another multiresistant bacterium found in the hospital environment, which can be resistant to penicillin, vancomycin and linezolide. *Mycobacterium tuberculosis* is commonly resistant to isoniazid and to rifampicin. Other pathogens offer certain resistances, such as *Salmonella*, *Campylobacter* and *Streptococcus*.

It therefore becomes essential, from a public health point of view, to be able to identify such microorganisms, and such resistance mechanisms, as rapidly as possible.

In general, the search for microorganisms resistant to a treatment is carried out according to the following steps:
1. Taking a biological sample that may contain said microorganisms;
2. Seeding and incubating a culture medium (18 to 48 h) in order to induce exponential growth of the microorganisms;
3. Pinpointing, on the culture media, colonies of potentially significant microorganisms;
4. Characterizing the microorganism species;
5. Identifying the mechanisms of resistance of the microorganisms analyzed, their biological significance and, optionally, the appropriate therapy.

This succession of steps involves a considerable amount of time between taking the sample that may contain microorganisms and prescribing a treatment that is appropriate for the patient. Furthermore, the user must generally perform steps for transferring microorganims from a first medium to a second medium manually, which can induce problems, in particular, of contamination, but also risks to the handler's health.

By way of example, in order to detect the presence of broad-spectrum beta-lactamases (ESBLs) in strains of *Escherichia coli* and *Klebsiella pneumoniae*, use may be made of a diffusion technique as described in the publication by Jacoby & Han (J Clin Microbiol. 34(4): 908-11, 1996), which does not however give any information regarding the identification of the strains tested: it is possible to determine whether or not the bacterium is a ESBL-producing bacterium, but it is not possible to distinguish whether such a bacterium is an *Escherichia coli* or a *Klebsiella pneumoniae*.

Metabolic substrates are also used for detecting the presence of ESBLs or HL cases. In this respect, AES laboratories proposes a medium in a biplate combining a Drigalski medium with cefotaxim and a MacConkey medium with ceftazidime. The Drigalski and MacConkey media make it possible to reveal lactose acidification, a metabolism which is present in a very large number of enterobacterial species. However, such a medium only makes it possible to distinguish resistant bacteria from non-resistant bacteria, and does not make it possible to distinguish bacteria expressing a ESBL from those expressing an HL Case. Neither does this medium make it possible to identify specific bacterial species, nor does it make it possible, for example, to discriminate between *E. coli* bacteria and *K. pneumoniae* bacteria.

In the case of the detection of resistance mechanisms other than ESBL, mention may be made of patent application EP0954560, which relates to the search for Vancomycin-resistant enterococcal, by combining Vancomycin with a chromogenic media that reveals two enzymatic activities (ß-glucosidase and pyrrolidonyl arylamidase). However, this chromogenic medium makes it possible to determine only whether or not the vancomycin-resistant strains belong to the *Enterococcus* genus, but does not make it possible to identify the species or the resistance mechanisms involved, in particular if it is a question of an acquired or wild-type resistance.

Thus, the characterization of a species of microorganism, and then the identification of its resistance to a treatment, is long and laborious. If the laboratory gives the clinician a positive screen, whereas the isolate is in fact free of resistant microorganisms, this can lead to needless and inappropriate treatment. Conversely, not communicating a positive screen, which is subsequently confirmed, delays the setting of the isolation of the patient (and possibly an appropriate therapy) by one day. This shows the need for a rapid and reliable confirmation test.

The present invention therefore proposes to improve the prior art by providing a novel diagnostic tool which allows a gain in time, in reliability and in relevance with respect to the therapy implemented. Our invention makes it possible, in a single step, to identify the species of microorganisms present in a sample, and to determine their mechanism of resistance in order to propose a treatment appropriate to each patient. This invention is particularly suitable for discriminating various species of microorganisms, which have various mechanisms of resistance to various treatments, but all of which may be present in the same sample.

Before going any further in the disclosure of the invention, the following definitions are given in order to facilitate understanding of the invention:

The term "culture medium" is intended to mean a medium comprising all the elements required for the survival and/or the growth of microorganisms. The culture medium according to the invention may contain any possible additives, for instance: peptones, one or more growth factors, carbohydrates, one or more selective agents, buffers, one or more gelling agents, etc. This culture medium may be in liquid form or in gel form which is ready to use, i.e. ready for seeding in a tube or flask or on a Petri plate.

For the purpose of the present invention, the term "microorganism" covers gram-positive or gram-negative bacteria, yeasts and, more generally, organisms that are generally unicellular, invisible to the naked eye, which can be multiplied and handled in the laboratory.

By way of gram-negative bacteria, mention may be made of bacteria of the following genres: *Pseudomonas, Escherichia, Salmonella, Shigella, Enterobacter, Klebsiella, Serratia, Proteus, Campylobacter, Haemophilus, Morganella, Vibrio, Yersinia, Acinetobacter, Branhamella, Neisseria, Burkholderia, Citrobacter, Hafnia, Edwardsiella, Aeromonas, Moraxella, Pasteurella, Providencia,* and *Legionella*.

By way of gram-positive bacteria, mention may be made of bacteria of the following genre: *Enterococcus, Streptococcus, Staphylococcus, Bacillus, Listeria, Clostridium, Gardnerella, Kocuria, Lactococcus, Leuconostoc, Micrococcus, Mycobacteria* and *Corynebacteria*.

By way of yeasts, mention may be made of yeasts of the following genre: *Candida, Cryptococcus, Saccharomyces* and *Trichosporon*.

The term "biological sample" is intended to mean a clinical sample, derived from a specimen of biological fluid, or a food sample, derived from any type of food. This sample may thus be liquid or solid and mention may be made, in the nonlimiting manner, of a clinical blood, plasma, urine or faeces sample, nose, throat, skin, wound or cephalospinal fluid specimens, a food sample from water, from drinks such as milk or a fruit juice; from yoghurt, from meat, from eggs, from vegetables, from mayonnaise, from cheese; from fish, etc., a food sample derived from a feed intended for animals, such as, in particular, a sample derived from animal meals.

The term "mechanism of resistance" is intended to mean any type of device which allows a microorganism to render a treatment partially or completely ineffective on said microorganism, guaranteeing its survival. The mechanisms of resistance are generally divided up into three categories: deficient penetration of the antibiotic into the bacterium, inactivation or excretion of the antibiotic by means of bacterial enzymatic systems, and lack of affinity between the bacterial target and the antibiotic.

By way of indication, mention may in particular be made of mechanisms of resistance related to the expression of an enzyme belonging to the broad-spectrum β-lactamase group; of an enzyme belonging to the chromosomal high level class C cephalosporinase group; mechanisms of resistance to glycopeptides, preferably developed by bacteria belonging to the *Enterococcus* genus.

Mention will also be made of mechanisms of resistance to methicillin, penicillin, tetracycline, erythromycin, or vancomycin when the microorganism is a *Staphylococcus aureus* bacterium.

Mention will also be made of mechanisms of resistance to penicillin, vancomycin and linezolide when the microorganism is an *Enterococcus faecium* bacterium.

Mention will also be made of mechanisms of resistance to amphotericin B or to antifungals of the azole family when the microorganism is a yeast.

Finally, mention will be made of mechanisms of resistance to isoniazid and to rifampicin when the microorganism is a *Mycobacterium tuberculosis* bacterium.

The term "treatment" is intended to mean a treatment capable of preventing or reducing the growth of microorganisms derived from a patient. This treatment may comprise in particular antimicrobial compounds, such as antibiotics, for instance penicillins, conventional cephalosporins, broad-spectrum cephalosporins, monobactams, glycopeptides or aminosides, or such as antifungals or resistance-inhibiting compounds. It should be noted that this treatment can also comprise the isolation of the patient, thereby preventing propagation of the microorganism among other patients.

The term "substrate" which allows the detection of an enzymatic or metabolic activity is intended to mean any molecule capable of directing or indirectly generating a detectable signal due to an enzymatic or metabolic activity of the microorganism.

When this activity is an enzymatic activity, reference is then made to an enzymatic substrate. The term "enzymatic substrate" is intended to mean any substrate that can be hydrolyzed by an enzyme into a product that allows the direct or indirect detection of a microorganism. This substrate comprises in particular a first part that is specific for the enzymatic activity to be revealed and a second part that acts as a label, hereinafter referred to as labeling part. This labeling part may be chromogenic, fluorogenic, luminescent, etc. As chromogenic substrate suitable for solid supports (filter, agar, electrophoresis gel), mention may in particular be made of substrates based on indoxyl and its derivatives, and substrates based on hydroxyquinoline or esculin and their derivatives, which allow the detection of osidase and esterase activities. Mention may also be made of substrates based on nitrophenol and nitroaniline and derivatives, making it possible to detect osidase and esterase activities in the case of substrates based on nitrophenol, and peptidase activities in the case of substrates based on nitroaniline. Finally, mention may be made of substrates based on naphtol and naphtylamine and their derivatives, which make it possible to detect osidase and esterase activities via naphtol, and peptidase activities via naphtylamine. This substrate may allow, in particular, but in a nonlimiting manner, the detection of an enzymatic activity such as the activity of an osidase, peptidase, esterase, etc. The enzymatic substrate can also be a natural substrate of which the product of hydrolysis is detected directly or indirectly. As natural substrate, mention may in particular be made of tryptophan for detecting tryptophanase or desaminase activity, a cyclic amino acid (tryptophan, phenylalanine, histidine, tyrosine) for detecting desaminase activity, phosphatidyl inositol for detecting phospholipase activity, etc. When this activity is a metabolic activity, the substrate is then a metabolic substrate, such as a source of carbon or of nitrogen, coupled to an indicator that produces a coloration in the presence of one of the metabolic products.

According to a preferred embodiment of the invention, said first and/or second enzymatic or metabolic activity is an enzymatic activity preferably chosen from the enzymatic activities: beta-glucosidase, desaminase, beta-glucuronidase, beta-galactosidase, alpha-glucosidase, alpha-galactosidase, hexosaminidase, N-acetyl-hexosaminidase, phosphatase, esterase, and aminopeptidase.

For example, for detecting *E. coli*, use is preferably made of beta-glucuronidase or ß-galactosidase or tryptophanase or desaminase activity; for detecting *Proteus*, use is preferably made of desaminase activity; for detecting enterococci, use is preferably made of beta-glucosidase activity. For *Candida albicans*, hexosaminidase is preferred, for *Listeria monocytogenes*, phospholipase is preferred, for salmonellae, esterase is preferred, for *Pseudomonas aeruginosa*, esterase or ß-alanine aminopeptidase is preferred, for *Staphylococcus aureus* phosphatase or alpha-glucosidase is preferred.

The expression "marker for differentiating" two groups of microorganisms is intended to mean a compound which does not have the same properties on a first and on a second group.

This compound may thus be:
a specific substrate;
an inhibitor of a mechanism of resistance, which then makes it possible to inhibit the growth of the organisms developing a specific resistance, without any discrimination of the microorganism species.

In the case of the use of a specific substrate, use is preferably made of beta-glucuronidase, beta-galactosidase, tryptophanase or desaminase activity for detecting *E. coli*, use is preferably made of desaminase activity for detecting *Proteus*, use is preferably made of beta-glucosidase activity for detecting enterococci. For *Candida albicans*, hexosaminidase is preferred, for *Listeria monocytogenes*, phospholipase is preferred, for salmonellae, esterase is preferred, for *Pseudomonas aeruginosa*, esterase or ß-alanine aminopeptidase is preferred, for *Staphylococcus aureus*, phosphatase or alpha-glucosidase is preferred.

In the case of the use of an inhibitor of a mechanism of resistance, use is preferably made of:
clavulanic acid, tazobactam or sulbactam when the first group and/or the second group comprises a mechanism of resistance induced by an expression of β-lactamases. The clavulanic acid concentration in the medium is then preferably between 0.05 and 32 mg/l, preferably between 0.1 and 8 mg/l, and even more preferably between 0.25 and 6 mg/l;
cloxacillin or dicloxacillin when the first group and/or the second group comprises a mechanism of resistance induced by the expression of cephalosporinases.

The term "taxon" is intended to mean a group of microorganisms having a taxonomic unit. A taxon may be a family, a genus, a set of genre, a species, a set of species or a subspecies. By way of indication, mention may be made of enterobacteria, *Klebsiella, Escherichia, Enterobacter, Citrobacter, Serratia*, KESC (*Klebsiella, Enterobacter, Serratia, Citrobacter*), *Proteeae, Proteus, Morganella, Pseudomonas, Staphylococcus, Streptococcus, Enterococcus, Candida, Escherichia coli, Escherichia coli* O157:H7, *Klebsiella pneumoniae, Citrobacter freundii, Enterococcus faecalis, Enterococcus faecium, Staphylococcus aureus*, coagulase-negative staphylocoque, *Candida albicans, Candida glabrata, Candida krusei, Candida lusitaniae*.

The term "antimicrobial" is intended to mean any compound capable of preventing or slowing down the growth of a microorganism. This compound may be an antibiotic or an antifungal.

The term "antibiotic" is intended to mean any compound capable of preventing or slowing down the growth of a bacterium. By way of indication, mention may in particular be made of the antibiotics cefotaxime, ceftazidime, ceftriaxone, cefpodoxime, aztreonam, vancomycin, tobramycin and ciprofloxacin.

The term "antifungal" is intended to mean any compound capable of preventing or slowing down the growth of a yeast or of a mould. By way of indication, mention may in particular be made of amphotericin B, fluconazole, itraconazole, voriconazole and cycloheximide.

According to a preferred embodiment of the invention, when the antibiotic is
cefotaxime, the cefotaxime concentration in the medium is preferably between 0.25 and 8 mg/l, preferably between 1 and 2 mg/l;
ceftazidime, the ceftazidime concentration in the medium is preferably between 0.25 and 8 mg/l, preferably between 2 and 2.5 mg/l;

ceftriaxone, the ceftriaxone concentration in the medium is preferably between 0.25 and 8 mg/l, preferably between 1 and 2.5 mg/l;

cefpodoxime, the cefpodoxime concentration in the medium is preferably between 0.1 and 32 mg/l, preferably between 0.75 and 10 mg/l, and even more preferably between 1 and 6 mg/l;

aztreonam, the aztreonam concentration in the medium is preferably between 0.1 and 8 mg/l, preferably between 0.75 and 1.5 mg/l.

According to a specific embodiment of the invention, the medium comprises a combination of at least two antibiotics. Preferably, the combination of at least two antibiotics comprises cefotaxime and ceftazidime.

Irrespective of the embodiment of the invention, the medium may also comprise a dye. By way of indication of a dye, mention may be made of Evans blue, neutral red, sheep blood, horse blood, and opacifier such as titanium oxide, nitroaniline, malachite green, brilliant green, etc.

All the media may also comprise, in order to increase their sensitivity:
  at least one antimicrobial that is active against gram-positive bacteria, such as in particular linezolide or vancomycin;
  at least one antimicrobial that is active against yeasts, such as in particular voriconazole or amphotericin B.

In this respect, the invention relates to the use of a combination of two culture media for distinguishing at least three groups of microorganisms in a biological sample, comprising:
  a first group of microorganisms, belonging to a first taxon of microorganisms and comprising at least a first mechanism of resistance to a first treatment;
  a second group of microorganisms, belonging to a second taxon of microorganisms and comprising at least a second mechanism of resistance to a second treatment;
  a third group of microorganisms, that are not resistant to said first and second treatments,
said combination of two culture media comprising:
  a. at least a first substrate for detecting at least a first enzymatic or metabolic activity of said first group of microorganisms;
  b. at least two markers for differentiating the first group of microorganisms and the second group of microorganisms;
  c. at least one antimicrobial that is active on said third group of microorganisms.

Preferably, the medium comprises at least two markers for differentiating the first group of microorganisms and the second group of microorganisms, at least one of which is an inhibitor of said first or said second mechanism of resistance. The medium may also comprise at least two markers for differentiating the first group of microorganisms and the second group of microorganisms, which are each an inhibitor of said first or said second mechanism of resistance.

This first embodiment of the invention makes it possible to distinguish, in the same sample, a first and a second group comprising various species or various taxons of microorganisms, each of the two groups being resistant to a different treatment.

This embodiment of the invention thus makes it possible, for example, to distinguish, in the same sample, a first group comprising *E. coli* ESBL bacteria and a second group comprising KESC HL Case bacteria. In this specific case, the combination of two media may be the following:

At least a first substrate which makes it possible to identify *E. coli* bacteria, for example a glucuronidase substrate, such as 6-chloro-3-indolyl-ß-D-glucuronide, or a galactosidase substrate, such as 5-bromo-6-chloro-3-indolyl-ß-D-galactoside;

a first identification marker which is a glucosidase substrate, such as 5-bromo-4-chloro-3-indolyl-ß-D-glucoside, which makes it possible to identify KESC bacteria;

a second identification marker which is a resistance mechanism inhibitor, such as cloxacillin;

at least one antimicrobial which is an antibiotic, such as cefpodoxime.

Reference is made to a combination of 2 media, i.e. a first medium may comprise:
  a first substrate which makes it possible to identify *E. coli*, for example a glucuronidase substrate, such as 6-chloro-3-indolyl-ß-D-glucuronide or a galactosidase substrate, such as 5-bromo-6-chloro-3-indolyl-ß-D-galactoside;
  a first marker which is a resistance mechanism inhibitor, such as cloxacillin;
  an antimicrobial which is an antibiotic, such as cefpodoxime,
or the second medium comprises:
  a first substrate which makes it possible to identify *E. coli*, fix example a glucuronidase substrate, such as 6-chloro-3-indolyl-ß-D-glucuronide, or a galactosidase substrate, such as 5-bromo-6-chloro-3-indolyl-ß-D-galactoside;
  a first marker which is a glucosidase substrate, such as 5-bromo-4-chloro-3-indolyl-ß-D-glucoside, which makes it possible to identify KESC bacteria;
  an antimicrobial which is an antibiotic, such as ceftazidime.

Another alternative would be to use a first medium comprising:
  a first substrate which makes it possible to identify *E. coli*, for example a glucuronidase substrate, such as 6-chloro-3-indolyl-ß-D-glucuronide, or a galactosidase substrate, such as 5-bromo-6-chloro-3-indolyl-ß-D-galactoside;
  a first marker which is a glucosidase substrate, such as 5-bromo-4-chloro-3-indolyl-ß-D-glucoside, which makes it possible to identify KESC bacteria;
  an antimicrobial which is an antibiotic, such as aztreonam,
while the second medium comprises:
  a first substrate which makes it possible to identify *E. coli*, for example a glucuronidase substrate, such as 6-chloro-3-indolyl-ß-D-glucuronide, or a galactosidase substrate, such as 5-bromo-6-chloro-3-indolyl-ß-D-galactoside;
  a first marker which is a resistance mechanism inhibitor, such as clavulanic acid;
  an antimicrobial which is an antibiotic, such as ceftazidime.

Those skilled in the art will choose each medium so as to systematically obtain a combination according to the invention. The antimicrobial that is active on said third group is present in the two media. Those skilled in the art may in particular use a biplate, for readily comparing the two media on which the same biological sample has been deposited.

In this respect, the invention also relates to a biplate comprising a combination of two culture media, said combination comprising:
  a. at least a first substrate for detecting at least a first enzymatic or metabolic activity of said first group of microorganisms;

b. at least two markers for differentiating the first group of microorganisms and the second group of microorganisms;

c. at least one antimicrobial that is active on said third group of microorganisms, said antimicrobial being present on each side of the biplate.

This first embodiment of the invention is not limited to distinguishing between 3 groups of microorganisms, but may make it possible to distinguish between 4, 5 or even more groups of microorganisms. It is then necessary to add additional identification markers to the medium or media, in order to discriminate between the various groups.

In this respect, the invention also relates to a biplate comprising a combination of two culture media, said combination comprising:

for the first medium:
- a first substrate which makes it possible to identify *E. coli*, for example a glucuronidase substrate such as 6-chloro-3-indolyl-ß-D-glucuronide, or a galactosidase substrate, such as 5-bromo-6-chloro-3-indolyl-ß-D-galactoside, or a substrate which makes it possible to identify *Proteeae*, for example tryptophan;
- a first identification marker which is a glucosidase substrate, such as 5-bromo-4-chloro-3-indolyl-ß-D-glucoside;
- a second identification marker which is a resistance inhibitor, such as cloxacillin;
- at least one antimicrobial which is an antibiotic, such as cefpodoxime;

for the second medium:
- a first substrate which makes it possible to identify enterococci, for example a glucosidase substrate, such as 5-bromo-4-chloro-3-indolyl-ß-D-glucoside;
- a first identification marker which is another glucosidase substrate, such as methyl-α-glucoside;
- at least one antimicrobial which is an antibiotic, such as vancomycin.

The invention also relates to the use of a culture medium for distinguishing at least 3 groups of microorganisms in a biological sample, comprising:

a first group of microorganisms, belonging to a first taxon of microorganisms and comprising at least one mechanism of resistance to a treatment;

a second group of microorganisms, belonging to a second taxon of microorganisms, different than said first taxon, but comprising at least one mechanism of resistance to a treatment, identical to that of the first group;

a third group of microorganisms, that are not resistant to said treatment, said culture medium comprising:

a. at least a first substrate for detecting at least a first enzymatic or metabolic activity of said first group of microorganisms;

b. at least one marker for differentiating the first group of microorganisms and the second group of microorganisms, said marker being a substrate for detecting at least one enzymatic or metabolic activity of said second group of microorganisms;

c. at least one antimicrobial that is active on said third group of microorganisms.

This second embodiment of the invention makes it possible to distinguish, in the same sample, a first and a second group comprising various species or various taxons of microorganisms, but each of the two groups being resistant to the same treatment. In this specific embodiment of the invention, it is not necessary to use a combination of media, since a single medium comprising the characteristics as defined above is sufficient.

This embodiment of the invention thus makes it possible, for example, to distinguish, in the same sample, a first group comprising *E. coli* ESBL bacteria and a second group comprising KESC ESBL bacteria.

In this respect, the invention relates to a culture medium comprising:
- a first substrate for detecting a beta-glucosidase enzymatic activity, preferably 5-bromo-4-chloro-3-indolyl-ß-D-glucoside, at a concentration of between 25 and 500 mg/l, preferably between 40 and 150 mg/l;
- a second substrate for detecting methyl-alpha-glucoside metabolism, in the presence of a colored indicator, preferably neutral red, at a concentration of between 2 and 100 mg/l, preferably between 4 and 50 mg/l;
- an antimicrobial which is an antibiotic, preferably vancomycin, at a concentration of between 0.5 and 128 mg/l, preferably between 2 and 32 mg/l.

When the antibiotic is vancomycin, this medium is preferably used for distinguishing:
- a first group of enterococcal bacteria developing an acquired resistance against vancomycin;
- a second group of enterococcal bacteria developing a natural resistance against vancomycin;
- a third group of enterococcal bacteria that are not resistant to vancomycin.

The invention also relates to a culture medium comprising:
- a first substrate for detecting a hexosaminidase enzymatic activity, preferably 5-bromo-4-chloro-3-indolyl-N-acetyl-ß-D-glucosaminide, and a concentration between 25 and 500 mg/l, preferably between 40 and 150 mg/l;
- a second substrate for detecting a beta-glucosidase activity, preferably 6-chloro-3-indolyl-ß-D-glucoside, at a concentration of between 25 and 500 mg/l, preferably between 40 and 200 mg/l;
- an antimicrobial which is an antifungal, which is preferably amphotericin B (amphoB), at a concentration of between 0.5 and 64 mg/l, preferably between 1 and 16 mg/l, even more preferably between 1 and 8 mg/l.

When the antifungal is amphotericin B, this medium is preferably used to distinguish:
- a first group of yeasts comprising *Candida albicans* developing a resistance to amphoB;
- a second group of yeasts comprising *Candida tropicalis* and/or *C. lusitaniae* and/or *C. kefyr*, developing a resistance to amphoB;
- a third group of yeasts that are not resistant to amphoB.

The invention also relates to a culture medium comprising:
- a first substrate for detecting a hexosaminidase enzymatic activity, preferably 5-bromo-4-chloro-3-indolyl-N-acetyl-ß-D-glucosaminide, at a concentration of between 25 and 500 mg/l, preferably between 40 and 150 mg/l;
- a second substrate for detecting a phosphatase activity, preferably 5-bromo-6-chloro-3-indolylphosphate, at a concentration of between 25 and 750 mg/l, preferably between 40 and 200 mg/l;
- an antimicrobial which is an antifungal, which is preferably amphoB, at a concentration of between 0.5 and 64 mg/l, preferably between 1 and 16 mg/l, even more preferably between 1 and 8 mg/l.

When the antifungal is amphotericin B, this medium is preferably used to distinguish:
- a first group of yeasts comprising *Candida albicans* developing a resistance to amphoB;
- a second group of yeasts comprising *Candida tropicalis* and/or *C. glabrata* and/or *C. krusei*, developing a resistance to amphoB;
- a third group of yeasts that are not resistant to amphoB.

The invention also relates to a culture medium comprising:
- a first substrate for detecting the hexosaminidase enzymatic activity of said first group, preferably 5-bromo-4-chloro-3-indolyl-N-acetyl-ß-D-glucosaminide, at a concentration of between 25 and 500 mg/l, preferably of between 40 and 150 mg/l;
- a second substrate for detecting the beta-glucosidase activity of said second group, preferably 6-chloro-3-indolyl-ß-D-glucoside, at a concentration of between 25 and 500 mg/l, preferably between 40 and 200 mg/l;
- an antimicrobial which is an antifungal, preferably fluconazole, at a concentration of between 1 and 256 mg/l, preferably between 2 and 128 mg/l, even more preferably between 8 and 64 mg/l.

When the antifungal is fluconazole, this medium is preferably used to distinguish:
- a first group of yeasts comprising *Candida albicans* developing a resistance to fluconazole;
- a second group of yeasts, comprising *Candida tropicalis* and/or *C. lusitaniae* and/or *C. kefyr*, developing a resistance to fluconazole;
- a third group of yeasts that are not resistant to fluconazole.

The invention also relates to a culture medium comprising:
- a first substrate for detecting a hexosaminidase enzymatic activity, preferably 5-bromo-4-chloro-3-indolyl-N-acetyl-ß-D-glucosaminide, at a concentration of between 25 and 500 mg/l, preferably between 40 and 150 mg/l;
- a second substrate for detecting a phosphatase activity, preferably 5-bromo-6-chloro-3-indolylphosphate, at a concentration of between 25 and 750 mg/l, preferably between 40 and 200 mg/l;
- an antimicrobial which is an antifungal, which is preferably fluconazole, at a concentration of between 1 and 256 mg/l, preferably between 2 and 128 mg/l, even more preferably between 8 and 64 mg/l.

When the antifungal is fluconazole, this medium is preferably used to distinguish:
- a first group of yeasts comprising *Candida albicans* developing a resistance to fluconazole;
- a second group of yeasts, comprising *Candida tropicalis* and/or *C. glabrata* and/or *C. krusei*, developing a resistance to fluconazole;
- a third group of yeasts that are not resistant to fluconazole.

The invention also relates to a culture medium comprising:
- a first substrate for detecting a beta-glucuronidase enzymatic activity, preferably 6-chloro-3-indolyl-ß-D-glucuronide, at a concentration of between 25 and 750 mg/l, preferably between 40 and 300 mg/l, or a beta-galactosidase enzymatic activity, preferably 5-bromo-6-chloro-3-indolyl-ß-D-galactoside, at a concentration of between 25 and 500 mg/l, preferably between 40 and 150 mg/l;
- a second substrate for detecting a beta-glucosidase activity, preferably 5-bromo-4-chloro-3-indolyl-ß-D-glucoside, at a concentration of between 25 and 500 mg/l, preferably between 40 and 250 mg/l, or a tryptophanase or desaminase activity, preferably tryptophan, at a concentration of between 50 and 5000 mg/l, preferably between 250 and 2000 mg/l;
- an antimicrobial which is an antibiotic, preferably ceftazidime. The ceftazidime concentration in the medium is then preferably between 0.25 and 8 mg/l, preferably between 2 and 2.5 mg/l.

When the antibiotic is ceftazidime, this medium is preferably used to distinguish:
- a first group of *E. coli* ESBL or HL Case bacteria;
- a second group of KESC ESBL or HL Case bacteria;
- a third group of bacteria that are not resistant to beta-lactamines and to cephalosporins.

The invention also relates to a culture medium comprising:
- a first substrate for detecting a beta-glucuronidase or beta-galactosidase enzymatic activity, preferably 6-chloro-3-indolyl-ß-D-glucuronide, at a concentration of between 25 and 750 mg/l, preferably between 40 and 300 mg/l, or 5-bromo-6-chloro-3-indolyl-ß-D-galactoside, at a concentration of between 25 and 500 mg/l, preferably between 40 and 150 mg/l;
- a second substrate for detecting a beta-glucosidase activity, preferably 5-bromo-4-chloro-3-indolyl-ß-D-glucoside, at a concentration of between 25 and 500 mg/l, preferably between 40 and 250 mg/l, or a tryptophanase or desaminase activity, preferably tryptophan, at a concentration of between 50 and 5000 mg/l, preferably between 250 and 2000 mg/l;
- an antimicrobial which is an antibiotic, preferably cefpodoxime, at a concentration of between 0.5 and 32 mg/l, preferably between 0.75 and 10 mg/l, and even more preferably between 1 and 6 mg/l, and cloxacillin, at a concentration of between 10 and 2000 mg/l, preferably between 50 and 500 mg/l.

When the antibiotic is cefpodoxime, this medium is preferably used to distinguish:
- a first group of *E. coli* ESBL bacteria;
- a second group of KESC ESBL bacteria;
- a third group of bacteria that are not resistant to beta-lactamines.

The invention also relates to a culture medium comprising:
- a first substrate for detecting a beta-glucuronidase enzymatic activity, preferably 6-chloro-3-indolyl-ß-D-glucuronide, at a concentration of between 25 and 750 mg/l, preferably between 40 and 300 mg/l, or a beta-galactosidase enzymatic activity, preferably 5-bromo-6-chloro-3-indolyl-ß-D-galactoside, at a concentration of between 25 and 500 mg/l, preferably between 40 and 150 mg/l;
- a second substrate for detecting a beta-glucosidase activity, preferably 5-bromo-4-chloro-3-indolyl-ß-D-glucoside, at a concentration of between 25 and 500 mg/l, preferably between 40 and 250 mg/l, or a tryptophanase or desaminase activity, preferably tryptophan, at a concentration of between 50 and 5000 mg/l, preferably between 250 and 2000 mg/l;
- a combination comprising an antimicrobial and a resistance inhibitor. Preferably, this combination comprises ceftriaxone at a concentration of between 0.25 and 8 mg/l, preferably between 1 and 2.5 mg/l, and clavulanic acid at a concentration of between 0.05 and 32 mg/l, preferably between 0.1 and 8 mg/l, and even more preferably between 0.5 and 6 mg/l.

This medium is preferably used to distinguish:
- a first group of *E. coli* HL Case bacteria;
- a second group of KESC HL Case bacteria;
- a third group of bacteria that are not resistant to cephalosporins.

The invention also relates to a culture medium comprising:
- a first substrate for detecting a beta-glucuronidase enzymatic activity, preferably 6-chloro-3-indolyl-ß-D-glucuronide, at a concentration of between 25 and 750 mg/l, preferably between 40 and 300 mg/l, or a beta-galactosidase enzymatic activity, preferably 5-bromo-6-chloro-3-indolyl-ß-D-galactoside, at a concentration between 25 and 500 mg/l, preferably between 40 and 150 mg/l;
- a second substrate for detecting a beta-glucosidase activity, preferably 5-bromo-4-chloro-3-indolyl-ß-D-glucoside, at a concentration of between 25 and 500 mg/l, preferably between 40 and 250 mg/l, or a tryptophanase or desaminase activity, preferably tryptophan, at a concentration of between 50 and 5000 mg/l, preferably between 250 and 2000 mg/l;
- two antimicrobials, which are preferably two antibiotics, preferably cefpodoxime at a concentration of between 0.1 and 32 mg/l, preferably between 0.25 and 10 mg/l, and even more preferably between 0.5 and 4 mg/l, and aztreonam at a concentration of between 0.1 and 8 mg/l, preferably between 0.5 and 1.5 mg/l.

This medium is preferably used to distinguish:
- a first group of *E. coli* ESBL or HL Case bacteria;
- a second group of KESC ESBL or HL Case bacteria;
- a third group of bacteria that are not resistant to beta-lactamines and/or to cephalosporins.

The invention also relates to a culture medium comprising:
- at least a first substrate for detecting alpha-glucoside metabolism or for detecting alpha-glucosidase activity, preferably methyl-α-glucoside, at a concentration of between 1 and 50 g/l, preferably between 5 and 20 g/l, or 5-bromo-4-chloro-3-indolyl-α-D-glucoside, at a concentration of between 25 and 500 mg/l, preferably between 40 and 250 mg/l, or 5-bromo-4-chloro-3-indolyl-N-methyl-α-D-glucoside, at a concentration of between 25 and 500 mg/l, preferably between 40 and 250 mg/l;
- at least a second substrate for detecting a second activity different than alpha-glucoside metabolism or the alpha-glucosidase activity, preferably 5-bromo-4-chloro-3-indolyl-ß-D-glucoside, at a concentration of between 25 and 500 mg/l, preferably between 40 and 250 mg/l, or 6-chloro-3-indolyl-ß-D-glucoside, at a concentration of between 25 and 500 mg/l, preferably between 40 and 250 mg/l, or alizarine-ß-D-galactoside, at a concentration of between 10 and 500 mg/l, preferably between 20 and 250 mg/l, or 5-bromo-6-chloro-3-indolyl-ß-D-glucoside, at a concentration of between 25 and 500 mg/l, preferably between 40 and 250 mg/l, or 5-bromo-6-chloro-3-indolyl-ß-D-galactoside, at a concentration of between 25 and 500 mg/l, preferably between 40 and 250 mg/l, or 6-chloro-3-indolyl-ß-D-galactoside, at a concentration of between 25 and 500 mg/l, preferably between 40 and 250 mg/l. Preferably, this second substrate makes it possible to detect a beta-glucosidase or beta-galactosidase activity; and
- at least one antimicrobial, preferably an antibiotic, such as vancomycin, at a concentration of between 0.5 and 128 mg/l, preferably between 2 and 32 mg/l.

When the antibiotic is vancomycin, this medium is preferably used to distinguish:
- a first group of vancomycin-resistant microorganisms, comprising *Enterococcus faecalis* and *Enterococcus faecium*;
- a second group of vancomycin-resistant microorganisms, comprising *Enterococcus casseliflavus* and *Enterococcus gallinarum*;
- a third group of microorganisms that are not resistant to vancomycin.

In this case, the first substrate is preferably methyl-α-glucoside, the second substrate is preferably 5-bromo-4-chloro-3-indolyl-ß-D-glucoside or 6-chloro-3-indolyl-ß-D-glucoside, and the antimicrobial is preferably vancomycin.

This medium is also preferably used to distinguish:
- a first group of vancomycin-resistant microorganisms, comprising *Enterococcus faecalis*;
- a second group of vancomycin-resistant microorganisms, comprising *Enterococcus faecium*;
- a third group of microorganisms that are not resistant to vancomycin or that express a natural resistance (*E. casseliflavus* and *E. gallinarum*).

In this case, the first substrate is preferably 5-bromo-4-chloro-3-indolyl-N-methyl-α-D-glucoside or 5-bromo-4-chloro-3-indolyl-α-D-glucoside, the second substrate is preferably 6-chloro-3-indolyl-ß-D-glucoside or alizarins-ß-D-galactoside or 5 bromo-6-chloro-3-indolyl-ß-D-glucoside or 5-bromo-6-chloro-3-indolyl-ß-D-galactoside or 6-chloro-3-indolyl-β-D-galactoside, and the antimicrobial is preferably vancomycin.

This medium is also preferably used to distinguish:
- a first group of vancomycin-resistant microorganisms, comprising *Enterococcus faecalis* and *Enterococcus faecium*;
- a second group of microorganisms, comprising *Staphylococcus aureus*, that are intermediately resistant or resistant to vancomycin;
- a third group of microorganisms that are not resistant to vancomycin.

In this case, the first substrate is preferably 5-bromo-4-chloro-3-indolyl-N-methyl-α-D-glucoside or 5-bromo-4-chloro-3-indolyl-α-D-glucoside, the second substrate is preferably 6-chloro-3-indolyl-ß-D-glucoside or 5-bromo-6-chloro-3-indolyl-ß-D-glucoside, and the antimicrobial is preferably vancomycin.

The table below makes it possible to distinguish the appropriate combinations of substrates and antimicrobial according to the species that it is desired to detect:

| 1st group of microorganisms | 2nd group of microorganisms | 3rd group of microorganisms | 1st substrate | 2nd substrate | Antimicrobial |
| --- | --- | --- | --- | --- | --- |
| *E. faecalis* and *E. faecium*, resistant to vancomycin | *E. casseliflavus* and *E. gallinarum*, resistant to vancomycin | Microorganisms that are not resistant to vancomycin | Methyl-α-glucoside | 5-bromo-4-chloro-3-indolyl-β-D-glucoside or 6-chloro- | vancomycin |

-continued

| 1st group of microorganisms | 2nd group of microorganisms | 3rd group of microorganisms | 1st substrate | 2nd substrate | Antimicrobial |
|---|---|---|---|---|---|
| E. faecalis, resistant to vancomycin | E. faecium, resistant to vancomycin | Microorganisms that are not resistant to vancomycin or that express a natural resistance (E. casseliflavus and E. gallinarum) | 5-bromo-4-chloro-3-indolyl-N-methyl-α-D-glucoside or 5-bromo-4-chloro-3-indolyl-α-D-glucoside | 3-indolyl-β-D-glucoside 6-chloro-3-indolyl-β-D-glucoside or alizarine-β-D-galactoside or 5-bromo-6-chloro-3-indolyl-β-D-glucoside or 5-bromo-6-chloro-3-indolyl-β-D-galactoside or 6-chloro-3-indolyl-β-D-galactoside | vancomycin |
| E. faecalis and E. faecium, resistant to vancomycin | S. aureus, resistant to vancomycin | Microorganisms that are not resistant to vancomycin | 5-bromo-4-chloro-3-indolyl-N-methyl-α-D-glucoside or 5-bromo-4-chloro-3-indolyl-α-D-glucoside | 6-chloro-3-indolyl-β-D-glucoside or 5-bromo-6-chloro-3-indolyl-β-D-glucoside | vancomycin |

It may be relevant to also adjust the vancomycin concentration, preferably to between 0.5 and 12 mg/l.

The invention also relates to a culture medium comprising:
- an antimicrobial, preferably an antibiotic such as cloxacillin;
- a resistance mechanism inhibitor, such as preferably a 3rd-generation cephalosporin chosen from cefotaxime, ceftazidime, cefpodoxime and ceftriaxone.

This medium is also preferably used to detect ESBL bacteria.

The second embodiment of the invention is not limited to distinguishing 3 groups of microorganisms, but can make it possible to distinguish 4, 5 or even more groups of microorganisms. It is then necessary to add, to the medium, markers for identification between the various groups.

In this respect, the invention also relates to a culture medium comprising:
- a first substrate for detecting a beta-glucuronidase enzymatic activity, preferably 6-chloro-3-indolyl-ß-D-glucuronide, at a concentration of between 25 and 750 mg/l, preferably between 40 and 300 mg/l, or a beta-galactosidase enzymatic activity, preferably 5-bromo-6-chloro-3-indolyl-ß-D-galactoside, at a concentration of between 25 and 500 mg/l, preferably of between 40 and 150 mg/l;
- a second substrate for detecting a beta-glucosidase, preferably 5-bromo-4-chloro-3-indolyl-ß-D-glucoside, at a concentration of between 25 and 500 mg/l, preferably between 40 and 250 mg/l;
- a combination of antimicrobials, preferably a combination of antibiotics such as
  - cefpodoxime at a concentration of between 0.5 and 32 mg/l, preferably between 0.75 and 10 mg/l, and even more preferably between 1 and 6 mg/l;
  - cloxacillin at a concentration of between 10 and 2000 mg/l, preferably between 50 and 500 mg/l;
  - vancomycin at a concentration of between 0.5 and 128 mg/l, preferably between 2 and 32 mg/l; and
  - amphoB at a concentration of between 0.5 and 64 mg/l, preferably between 1 and 16 mg/l, even more preferably between 1 and 8 mg/l;
- a third substrate for detecting a desaminase activity, such as histidine, phenylalanine, tryptophan or tyrosine, at a concentration of between 50 and 5000 mg/l, preferably between 250 and 2000 mg/l.

This medium may also comprise a fifth antibiotic, which is cefsulodine, at a concentration of between 0.5 and 64 mg/l, preferably between 1 and 16 mg/l.

This medium is preferably used to distinguish:
- a first group of E. coli ESBL bacteria;
- a second group of KESC ESBL bacteria;
- a third group of bacteria that are not resistant to beta-lactamines and/or to cephalosporins;
- a fourth group of Proteeae ESBL bacteria.

Similarly, the invention also relates to a culture medium comprising:
- at least a first substrate for detecting alpha-glucoside metabolism or for detecting alpha-glucosidase activity, preferably 5-bromo-4-chloro-3-indolyl-α-D-glucoside, at a concentration of between 25 and 500 mg/l, preferably between 40 and 250 mg/l, or 5-bromo-4-chloro-3-indolyl-N-methyl-α-glucoside, at a concentration of between 25 and 500 mg/l, preferably between 40 and 250 mg/l;
- at least a second substrate for detecting a second activity different than alpha-glucoside metabolism or the alpha-glucosidase activity, preferably 6-chloro-3-indolyl-ß-D-glucoside, at a concentration of between 25 and 500 mg/l, preferably between 40 and 250 mg/l, or 6-chloro-3-indolyl-β-D-galactoside, at a concentration of between 25 and 500 mg/l, preferably between 40 and 250 mg/l, or alizarine-β-galactoside, at a concentration of between 10 and 500 mg/l, preferably between 20 and 250 mg/l, or 5-bromo-6-chloro-3-indolyl-ß-D-glucoside, at a concentration of between 25 and 500 mg/l, preferably between 40 and 250 mg/l, or 5-bromo-6-chloro-3-indolyl-ß-D-galactoside, at a concentration of between 25 and 500 mg/l, preferably between 40 and 250 mg/l, or 6-chloro-3-indolyl-ß-D-galactoside, at a concentration of between 25 and 500 mg/l, preferably between 40 and 250 mg/l. Preferably, this second substrate makes it possible to detect a beta-glucosidase or beta-galactosidase activity; and a combination of antimicrobials, preferably a combination of antibiotics such as
- a vancomycin at a concentration of between 0.5 and 128 mg/l, preferably between 2 and 32 mg/l;
- aztreonam at a concentration of between 1 and 150 mg/l, preferably between 4 and 60 mg/l;
- colistine at a concentration of between 1 and 100 mg/l, preferably between 2 and 20 mg/l;
- amphotericin B at a concentration of between 0.5 and 50 mg/l, preferably between 1 and 15 mg/l.

When one of the antibiotics is vancomycin, this medium is preferably used to distinguish:
- a first group of vancomycin-resistant microorganisms, comprising *Enterococcus faecium*,
- a second group of vancomycin-resistant microorganisms, comprising *Enterococcus faecalis*,
- a third group of microorganisms that are not resistant to vancomycin.

This medium is also preferably used to distinguish:
- a first group of vancomycin-resistant microorganisms, comprising *Enterococcus faecium*,
- a second group of microorganisms, comprising *Staphylococcus aureus*, that are intermediately resistant or resistant to vancomycin;
- a third group of microorganisms that are not resistant to vancomycin.

The combinations of substrates according to the groups of microorganisms that it is desired to identify are presented, for example, in the table on page 21. By using an appropriate combination of antimicrobials, it is possible to distinguish not only three groups of microorganisms, but also 4, 5 or even more groups of microorganisms.

The invention also relates to the use of a combination of two culture media for distinguishing at least 3 groups of microorganisms in a biological sample, comprising:
- a first group of microorganisms, belonging to a first species of microorganisms and comprising a first mechanism of resistance to a first treatment;
- a second group of microorganisms, belonging to a species of microorganisms that is identical to that of said first group of microorganisms, but comprising a second mechanism of resistance to a second treatment, different than that of said first group;
- a third group of microorganisms that are not resistant to said first and second treatment, said combination of two culture media comprising:
a. at least a first substrate for detecting at least a first enzymatic or metabolic activity of said first group of microorganisms;
b. at least one marker for differentiating the first group of microorganisms and the second group of microorganisms, said marker being an inhibitor of the mechanism of resistance to the first treatment and/or to the second treatment;
c. at least one antimicrobial that is active on said third group of microorganisms.

This third embodiment of the invention makes it possible to distinguish, in the same sample, a first and a second group comprising the same species of microorganisms or the same taxon, each of the two groups being resistant to different treatments.

This embodiment of the embodiment thus makes it possible, for example, to distinguish, in the same sample, a first group comprising *E. coli* ESBL bacteria, and a second group comprising *E. coli* HL Case bacteria. In this specific case, the combination of two media may be the following:
- at least a first substrate which makes it possible to identify *E. coli*, for example a beta-glucuronidase substrate, such as 6-chloro-3-indolyl-ß-D-glucuronide, or a beta-glucosidase substrate, such as 5-bromo-6-chloro-3-indolyl-ß-D-galactoside;
- a first identification marker which is a resistant mechanism inhibitor, preferably cloxacillin;
- a second identification marker which is another resistance mechanism inhibitor, preferably clavulanic acid;
- at least one antimicrobial which is cefpodoxime.

Reference is made to a combination of 2 media, i.e. a first medium may comprise:
- a first substrate which makes it possible to identify *E. coli*, which is 6-chloro-3-indolyl-ß-D-glucuronide;
- a first marker which is a resistance mechanism inhibitor, preferably cloxacillin;
- an antimicrobial, preferably an antibiotic, preferably cefpodoxime.

while the second medium comprises:
- a first substrate which makes it possible to identify *E. coli*, such as 6-chloro-3-indolyl-ß-D-glucuronide;
- a second marker which is another resistance mechanism inhibitor, preferably clavulanic acid;
- an antimicrobial, preferably an antibiotic, preferably cefpodoxime.

Another alternative would be to use a first medium comprising:
- a first substrate which makes it possible to identify *E. coli*, which is 5-bromo-6-chloro-3-indolyl-ß-D-galactoside;
- a first marker which is a substrate for a desaminase or for a tryptophanase, preferably tryptophan;
- an antimicrobial, preferably an antibiotic, preferably cefpodoxime, or the second medium comprises;
- a first substrate which makes it possible to identify *E. coli*, which is 6-chloro-3-indolyl-ß-D-glucuronide;
- a second marker which is a resistance mechanism inhibitor, preferably clavulanic acid;
- an antimicrobial, preferably an antibiotic, which is preferably ceftazidime.

Those skilled in the art will choose each medium in such a way as to systematically obtain a combination according to the invention. The antimicrobial that is active on said third group is present in the two media. Those skilled in the art may in particular use a biplate, which makes it possible to readily compare the two media on which the same biological sample would have been deposited.

In this respect, the invention also relates to a biplate comprising a combination of two culture media, said combination comprising:
a. at least a first substrate for detecting at least a first enzymatic or metabolic activity of said first group of microorganisms;
b. at least one marker for differentiating the first group of microorganisms and the second group of microorganisms, said marker being an inhibitor of the mechanism of resistance to the first treatment and/or to the second treatment;
c. at least one antimicrobial that is active on said third group of microorganisms.

This third embodiment of the invention is not limited to distinguishing 3 groups of microorganisms, but may make it possible to distinguish 4, 5 or even more groups of microorganisms. It is then necessary to add additional identification markers to the medium, in order to discriminate the various groups.

In this respect, the invention relates to a biplate comprising a combination of two culture media, said combination comprising:

for the first medium,
a first substrate which makes it possible to identify *E. coli*, for example a glucuronidase substrate, such as 6-chloro-3-indolyl-ß-D-glucuronide, or a galactosidase substrate, such as 5-bromo-6-chloro-3-indolyl-ß-D-galactoside;
a second substrate which makes it possible to identify *Proteeae*, for example a substrate for a desaminase or for a tryptophanase, such as tryptophan;
a third substrate which makes it possible to identify the KESC group, for example a glucosidase substrate, such as 5-bromo-4-chloro-3-indolyl-ß-D-glucoside;
a marker for differentiating between ESBL strains and HL Case strains, preferably a resistance inhibitor, preferably clavulanic acid;
at least one antimicrobial which is preferably an antibiotic, preferably ceftazidime;

for the second medium:
a first substrate which makes it possible to identify *E. coli*, for example a glucuronidase substrate, such as in particular 6-chloro-3-indolyl-ß-D-glucuronide, or a galactosidase substrate, such as in particular 5-bromo-6-chloro-3-indolyl-ß-D-galactoside;
a second substrate which makes it possible to identify *Proteeae*, for example a substrate for a desaminase or for a tryptophanase, such as tryptophan;
a third substrate which makes it possible to identify the KESC group, for example a glucosidase substrate, such as in particular 5-bromo-4-chloro-3-indolyl-ß-D-glucoside;
at least one antimicrobial, preferably an antibiotic, preferably ceftriaxone.

The examples below are given by way of explanation and are no way limiting in nature, They will make it possible to understand the invention more fully.

EXAMPLE 1

The example below is based on the phenotypic detection of ESBLs using the reduction of susceptibility of these strains to antibiotics and their sensitivity to combinations with β-lactamases inhibitors. For this, a biplate of CPS ID 3 base (chromogenic medium for detecting microorganisms in urine, and sold by bioMérieux under the reference 43541) with one half-agar containing an antibiotic and one half-agar containing an antibiotic/β-lactamases inhibitor combination was used.

1. Choice of Strains

In the context of the manipulations carried out, for evaluating the activity of the antibiotics active on gram-negative bacilli, various species of enterobacteria (*Escherichia coli, Enterobacter aerogenes, Klebsiella pneumoniae, Serratia marcescens, Proteus mirabilis*) and of nonfermenting gram-negative bacilli (*Pseudomonas aeruginosa*), capable of producing ESBLs, were used. ESBL-positive strains, high level cephalosporinase-producing strains (HL Case) and wild-type strains are compared in the trials.

For the manipulations regarding the antibiotics active on gram-positive bacteria, strains of gram-positive cocci (*Staphylococcus aureus, Staphylococcus saprophyticus, Staphylococcus epidermidis, Enterococcus faecalis, Enterococcus faecium, Streptococcus agalactiae*) and of gram-positive bacilli (*Lactobacillus* spp) were tested.

For the trials intended to evaluate the activity of the antifungals, various strains of yeasts (*Candida albicans, Candida glabrata, Candida tropicalis, Candida krusei, Candida dubliniensis, Saccharomyces cerevisiae, Geotrichum capitatum*) were used.

2. Preparation of Media

The medium used was a CPS ID3 medium (reference 43541) also comprising at least one antibiotic and at least one resistance mechanism inhibitor.

The composition of the media tested was the following:

|  | Chromogenic substrate | Antibiotic | Resistance inhibitor |
|---|---|---|---|
| Medium A | 6-chloro-3-indolyl-ß-D-glucuronide 5-bromo-4-chloro-3-indolyl-ß-D-glucoside Tryptophan FeCl$_3$ Total: 1.73 g/l | Cefotaxime 1 mg/l | |
| Medium B | 6-chloro-3-indolyl-ß-D-glucuronide 5-bromo-4-chloro-3-indolyl-ß-D-glucoside Tryptophan FeCl$_3$ Total: 1.73 g/l | Ceftazidime 1.5 mg/l | 0.25 mg/l clavulanic acid |

Osmosed water is added and the whole is homogenized and melted in a waterbath at 100° C. The base medium is dispensed into flasks, the number of which corresponds to the total number of media to be tested during the process. The flasks are then autoclaved for 15 min at 121° C. The media are brought back to and kept molten at 55±3° C. in a waterbath, in order to sterilely add the thermolabile additives (sterilized beforehand by filtration through 0.22 µm). The media are then poured into biplates 90 mm in diameter (i.e. approximately 9.5 ml/half-plate), and left on a flat surface so that they can set. The surface of the agars is then dried under a laminar flow hood for 30 min.

3. Inoculation of Media

An inoculum of 0.5 McF is prepared, in physiological saline, from 24-hour precultures at 36° C.±2° C. in an aerobic atmosphere on TSA medium, and then 1 µl of this suspension is transferred into 5 ml of physiological saline. In order to obtain a sufficient number of isolated colonies, a range of inocula made it possible to determine that the optimal amount of bacteria to be inoculated was from $10^3$ to $10^4$ CFU/ml. The inoculation is carried out directly on the two half-agars using a sterile swab. The cultures are then incubated at 37° C. in an aerobic atmosphere.

4. Reading of Media:

the readings are carried out at 18 hours (±30 min), 24 h (±1 h) and 48 h (±4 h). The density and the size of the colonies, and the appearance, the color and the coloration intensities of the mass and of the isolated colonies were observed, according to the following reading scales 1 to 3:0: no growth; 0.1: trace of growth; 0.25: colonies of diameter <0.5 mm; 0.5: colonies of 0.5 mm in diameter; 0.75:0.5 mm<diameter<1 mm; 1: colonies of 1 mm in diameter; 1.25:1 mm<diameter<1.5 mm; 1.5: colonies 1.5 mm in diameter; 2: colonies 2 mm in diameter; 3: colonies of diameter >2 mm.

5. Results:

a) Screening of Antibiotics

The 5 antibiotics recommended by the NCCLS (National Committee for Clinical Laboratory Standards) were tested. For each product tested, a range was prepared in order to determine the concentrations that make it possible to inhibit the wild-type strains of the enterobacteria tested, without affecting the growth of the ESBL-positive strains or the HL Case-positive strains.

The concentrations selected are listed in table III hereinafter.

TABLE III

Limiting values of the concentrations of antibiotics that allow inhibition of the wild-type strains of the enterobacteria tested, without affecting the growth of the ESBL-positive strains under the conditions tested

|  | Low value | High value |
| --- | --- | --- |
| Cefotaxime | 1 mg/l | 2 mg/l |
| Ceftazidime | 2 mg/l | 2.5 mg/l |
| Ceftriaxone | 1 mg/l | 2.5 mg/l |
| Cefpodoxime | 2 mg/l | 10 mg/l |
| Aztreonam | 1 mg/l | 1.5 mg/l |

The low value corresponds to the minimum concentration of the antibiotic required to inhibit the wild-type strains of the enterobacteria tested. The high value corresponds to the maximum concentration of the antibiotic that can be used without affecting the growth of the ESBL-positive strains tested.

At these concentrations, the separation of the wild-type and resistant strains is satisfactory, and the expression of the enzymatic activities on the CPS ID 3 medium is compliant.

In addition, it should be noted that ceftazidime is the only antibiotic tested and used in the detection of ESBLs which showed an activity on the wild-type strains of *P. aeruginosa*. A range was prepared in order to define the minimum concentration for complete inhibition of these strains, and the limiting value is 1.5 mg/l.

The addition of antibiotics had no effect on the expression of the bacterial enzymatic activities on the chromogenic medium. The groups of microorganisms were separated and identified both on control CPS ID 3 medium and on the media comprising the antibiotics as described above.

b) Screening of ß-lactamase Inhibitors

Three β-lactamases inhibitors (BLIs), i.e. clavulanic acid, tazobactam and sulbactam, were used. A range was prepared for each one, in the presence of cefotaxime, in order to determine the optimum concentration for inhibiting the ESBL-positive strains without impairing the growth of the HL Case strains.

Clavulanic acid appeared to be the most effective BLI in the presence of cefotaxime. Tazobactam and sulbactam required concentrations of greater than 2 mg/l in order to inhibit the ESBL-positive strains, whereas clavulanic acid was more active at much lower concentrations, over a broad operating range (from 0.1 to 8 mg/l when it is used in combination with cefotaxime).

Each antibiotic (cefotaxime, ceftazidime, ceftriaxone, cefpodoxime, aztreonam) was tested in the presence of a range of clavulanic acid in order to define the most effective combinations. The combinations selected are listed in table IV below.

TABLE IV

Selected combinations of antibiotics and of clavulanic acid (CA) that inhibit the ESBL-positive enterobacterial strains tested, but allow the HL Case-positive strains to grow

| Cefotaxime | 2 mg/l | +CA | 0.1 mg/l |
| Ceftazidime | 2.5 mg/l | +CA | 2 mg/l |
| Ceftriaxone | 2 mg/l | +CA | 0.25 mg/l |

TABLE IV-continued

Selected combinations of antibiotics and of clavulanic acid (CA) that inhibit the ESBL-positive enterobacterial strains tested, but allow the HL Case-positive strains to grow

| Cefpodoxime | 9 mg/l | +CA | 0.25 mg/l |
| Aztreonam | 1 mg/l | +CA | 0.5 mg/l |

The results obtained using a biplate containing the antibiotic alone on one side and the antibiotic+clavulanic acid combination on the other side are listed in table V.

TABLE V

|  | Antibiotic alone | Antibiotic + clavulanic acid |
| --- | --- | --- |
| Wild-type *E. coli* |  |  |
| ESBL-positive *E. coli* | Pink colonies |  |
| HL Case-positive *E. coli* | Pink colonies | Pink colonies |
| Wild-type Proteeae |  |  |
| ESBL-positive Proteeae | Brown colonies |  |
| HL Case-positive Proteeae | Brown colonies | Brown colonies |
| Wild-type KESC |  |  |
| ESBL-positive KESC | Green colonies |  |
| HL Case-positive KESC | Green colonies | Green colonies |

The addition of β-lactamase inhibitors had no effect on the expression of the bacterial enzymatic activities on the chromogenic medium. The groups of microorganisms were separated and identified both on control CPS ID 3 medium and on the media comprising β-lactamase inhibitors.

c) Combination of Antibiotics

Given the relative activities of the antibiotics and of clavulanic acid, the following were combined:

cefotaxime (antibiotic active on ESBL-positive strains in combination with the lowest concentration of clavulanic acid), ceftazidime (antibiotic active on wild-type strains of *P. aeruginosa*), and clavulanic acid, so as to be able to inhibit, firstly, the wild-type strains (including those of pyocyanic bacillus), and the ESBL-positive strains of the enterobacteria tested by the addition of the BIL.

Such a combination was tested on strains of *P. aeruginosa*; this species is naturally resistant to cefotaxime but sensitive to ceftazidime. When 1.5 mg/l of CAZ (ceftazidime), 1 mg/l of CTX (cefotaxime) and 0.25 mg/l of CA (clavulanic acid) were combined, all the wild-type strains and the ESBL-positive strains of the enterobacteria tested were inhibited and only the collection of HL Case strains and the ESBL-positive *P aeruginosa* strains grew. It involves a biplate with CAZ alone on one side and CTX plus clavulanic acid on the other.

The addition of these combinations of antibiotics had no effect on the expression of the bacterial enzymatic activities on the chromogenic medium. The groups of microorganisms were separated and identified both on control CPS ID 3 medium and on the media comprising such combinations of antibiotics.

d). Dye Assay

A medium according to the invention was also employed for use in a biplate, one of the sides containing an antibiotic, and the second containing another antibiotic or a combination of antibiotics. Given that the same CPS ID 3 medium base is used on either side, these two sides were differentiated by the presence of a dye.

The dye tested, Evans blue, gives the medium a green color. The coloration has made it possible to readily differentiate the 2 sides of the biplate without affecting the fertility of the medium, or impairing the reading of the enzymatic activities of the colonies. After having produced a range of Evans blue, added before or after autoclaving, the values selected were the following:

1.5 or 2 mg/l if the dye is added after autoclaving.
between 2 and 5 mg/l if it is added before autoclaving.

e). Inhibition of Gram-Positive Bacteria

ESBLs are a mechanism of resistance to β-lactamines that is found only in gram-negative bacilli; it is therefore advisable to inhibit the gram-positive bacteria via the medium. Two antibiotics, linezolide and vancomycin, were used in the medium according to the invention for the purpose of inhibiting the sensitive gram-positive bacteria.

For vancomycin, under the conditions tested, a concentration between 2 and 32 mg/l, and in particular 2 to 5 mg/l, makes it possible to inhibit the sensitive gram-positive bacteria without interfering with the detection of the ESBL bacteria.

For linezolide, under the conditions tested, a concentration between 2 and 64 mg/l, and in particular 4 to 16 mg/l, makes it possible to inhibit the sensitive gram-positive bacteria without interfering with the detection of the ESBL bacteria.

The inhibition of the gram-positive bacteria made it possible to improve the detection of the ESBL bacteria in polymicrobial samples and the specificity of their coloration.

f) Inhibition of Yeasts

A medium according to the invention can also comprise antifungals in order to inhibit the possible presence of yeasts which could grow on the medium and which could impair microorganism growth.

Two antifungals were therefore tested: voriconazole and amphotericin B.

For amphotericin B, under the conditions tested, a concentration between 1 and 32 mg/l, and in particular 2 to 8 mg/l, makes it possible to inhibit the sensitive yeasts without interfering with the detection of the ESBL bacteria.

For voriconazole, under the conditions tested, a concentration of between 1 and 64 mg/l, and in particular 4 to 16 mg/l, makes it possible to inhibit the sensitive gram-positive bacteria without interfering with the detection of the ESBL bacteria.

The inhibition of the yeasts made it possible to improve the detection of ESBL bacteria in polymicrobial samples and the specificity of their coloration.

6. Conclusion

These results demonstrate that the medium according to the invention makes it possible to isolate and apparently identify ESBL-producing bacteria, differentiating them from high level cephalosporinase-producing strains. The use of a biplate containing a cephalosporine alone on one side and a cephalosporine/clavulanic acid combination on the other, in a CPS ID 3 base, is particularly advantageous.

EXAMPLE 2

This second example is based on the phenotypic detection of ESBLs using the reduction of susceptibility to antibiotics of HL Cases to combinations with tobramycin or cloxacillin or dicloxacillin, and presents the use of a cephalosporine mentioned above (CTX, CAZ, CPD, CRO, ATM) in combination with a compound that inhibits cephalosporinases (cloxacillin, dicloxacillin and tobramycin). Such a medium makes it possible to inhibit bacteria which have a "natural" cephalosporinase, most of those which have only a high level cephalosporinase (HL Case), while at the same time allowing growth of ESBL bacteria.

1. Choice of Strains

In the context of the manipulations carried out, for evaluating the activity of antibiotics that are active on gram-negative bacilli, various species of enterobacteria (*Escherichia coil, Enterobacter aerogenes, Klebsiella pneumoniae, Proteus mirabilis*) and of nonfermenting gram-active bacilli (*Pseudomonas aeruginosa*) capable of producing ESBLs, were used. In the assays, ESBL-positive strains, strains producing high level cephalosporinase (HL Case) and wild-type strains are compared.

2. Preparation of the Medium

The medium used was a CPS ID3 medium (43541), also comprising:

ceftazidime at 2.5 mg/l and tobramycin at 2 mg/l (medium A) or ceftriaxone at 2 mg/l and cloxacillin at 150 mg/l (medium B) or cefpodoxime at 2 mg/l and dicloxacillin at a concentration of between 500 and 1000 mg/l (medium C).

Osmosed water is added and the whole is homogenized and melted in a waterbath at 100° C.

The basic medium is dispensed into flasks, the number of which corresponds to the total number of media to be tested during the process. The flasks are then autoclaved for 15 min at 121° C. The media are brought back to and kept molten at 55±3° C. in a waterbath, in order to sterilely add the thermolabile additives (sterilized beforehand by filtration through 0.22 μm). The media are then poured into plates 35 mm in diameter and left on a flat surface so that they can set. The surface of the agars is then dried under a laminar flow hood for 30 min.

3. Inoculation of Media

This step is carried out as described in example 1.

4. Reading of Media

This step is carried out as described in example 1

5. Results:

Medium A comprising ceftazidime and tobramycin made it possible to inhibit all the wild-type strains and all the HL Cases tested. Only the ESBL-positive strains were detected on this medium.

Medium B comprising ceftriaxone and cloxacillin made it possible to inhibit all the HL Cases and all the wild-type strains except HL Case and wild-type *P aeruginosa*, and grew only the majority of the ESBL-positive strains.

Medium C comprising cefpodoxime and di-cloxacillin made it possible to inhibit all the wild-type strains and the majority of the HL Cases, without affecting the growth of ESBL-positive strains.

EXAMPLE 3

This third example is based on the phenotypic detection of enterococci resistant to glycopeptides, with specific distinction of *Enterococcus faecalis* and *E. faecium*, using the reduction of susceptibility to antibiotics and the demonstration of an enzymatic activity: ß-glucosidase, and of a metabolic activity: Methyl-α-glucoside acidification.

1. Choice of Strains

In the context of the manipulations carried out, for evaluating the activity of the antibiotics active on enterococci, various species of *Enterococcus (Enterocoocccus faecalis, Enterococcus faecium, Enterococcus casseliflavus, Entero-*

*coccus gallinarum,*) were used. In the assays, strains resistant to glycopeptides (VRE) and wild-type strains are compared.

2. Preparation of the Medium

The medium used was a Columbia medium (51026), also comprising:

5-bromo-4-chloro-3-indolyl-ß-D-glucopyranoside (X-Glu) at 100 mg/l,
methyl-α-D-glucoside at 9 g/l,
neutral red at 25 mg/l,
bilial salts at 5 g/l,
vancomycin at 4 mg/l,
amphotericin B at 2 mg/l.

Osmosed water is added and the whole is homogenized and melted in a waterbath at 100° C. The basic medium is dispensed into flasks, the number of which corresponds to the total number of media to be tested during the process. The flasks are then autoclaved for 15 min at 121° C. The media are brought back to and kept molten at 55±3° C. in a waterbath, in order to sterilely add the thermolabile additives (sterilized beforehand by filtration through 0.22 μm). The media are then poured into plates 90 mm in diameter and left on a flat surface so that they can set. The surface of the agars is then dried under a laminar flow hood for 30 min.

3. Inoculation of Media

This step is carried out as described in example 1.

4. Reading of Media

This step is carried out as described in example 1.

5. Results:

On this medium, only the glycopeptide-resistant enterococcal strains develop and form colonies.

The resistant *E. faecalis* and *E. faecium* strains form green colonies, whereas those of *E. casseliflavus* and of *E. gallinarum* form blue-to-violet colonies.

This medium therefore makes it possible to differentiate these two groups of enterococci and to provide a suitable therapeutic response.

EXAMPLE 4

This fourth example is based on the phenotypic detection of glycopeptide-resistant enterococci, with specific distinction of *Enterococcus faecalis* and *E. faecium*, using the reduction of susceptibility to antibiotics and the demonstration of two enzymatic activities: α-glucosidase and β-galactosidase or β-glucosidase.

1. Choice of Strains

In the context of the manipulations carried out, for evaluating the activity of antibiotics active on enterococci, various species of Enterococcus (*Enterocoocccus faecalis, Enterococcus faecium, Enterococcus casseliflavus, Enterococcus gallinarum,*) were used. In the assays, strains resistant to glycopeptides (VRE) and wild-type strains are compared.

2. Preparation of the Medium

The media used were a Columbia medium (51026), also comprising:

5-bromo-4-chloro-3-indolyl-N-methyl-α-D-glucopyranoside (GreenA-α-Glu) at 150 mg/l,
6-chloro-3-indolyl-β-glucopyranoside (Rose-b-Glu [Pink-b-Glu]) at 200 mg/l, or:

5-bromo-4-chloro-3-indolyl-N-methyl-α-D-glucopyranoside (GreenA-α-Glu) at 150 mg/l,
alizarine-β-galactopyranoside at 50 mg/l
and vancomycin at 8 mg/l,
an amphotericin B at 4 mg/l,
and colistine at 2 mg/l,
and aztreonam at 32 mg/l.

Osmosed water is added and the whole is homogenized and melted in a waterbath at 100° C. The two basic media are dispensed into flasks. The flasks are then autoclaved for 15 min at 121° C. The media are brought back to and kept molten at 55±3° C. in a waterbath, in order to sterilely add the thermolabile additives (sterilized beforehand by filtration through 0.22 μm). The media are then poured into plates 90 mm in diameter and left on a flat surface so that they can set. The surface of the agars is then dried under a laminar flow hood for 30 min.

3. Inoculation of Media

This step is carried out as described in example 1.

4. Reading of Media

This step is carried out as described in example 1.

5. Results:

On the medium containing a substrate for α-glucosidase and for β-glucosidase, the resistant *E. faecium* strains form violet colonies, whereas the resistant *E. faecalis* strains form pink colonies. The *E. casseliflavus* and *E. gallinarum* strains (natural resistances) are inhibited due to the concentration of vancomycin.

This medium therefore makes it possible to differentiate these two groups of enterococci and to provide a suitable therapeutic response and also a follow-up of the local epidemiology.

On the medium containing a substrate for α-glucosidase and for β-galactosidase, the resistant *E. faecium* strains form violet colonies, whereas the resistant *E. faecalis* strains form green colonies. The *E. casseliflavus* and *E. gallinarum* strains (natural resistances) are inhibited due to the concentration of vancomycin.

This medium therefore makes it possible to differentiate these two groups of enterococci and to provide a suitable therapeutic response and a follow-up of the local epidemiology.

What is claimed is:

1. A method of detecting and distinguishing between any extended-spectrum β-lactamase-producing *E. coli* bacteria (ESBL *E. coli* bacteria) and any extended-spectrum β-lactamase-producing KESC bacteria (ESBL KESC bacteria) that are present on a culture medium, the method comprising:
   inoculating a culture medium with a biological sample, wherein the culture medium comprises:
      a first substrate for detecting beta-galactosidase activity;
      a second substrate for detecting beta-glucuronidase activity;
      a third substrate for detecting desaminase activity; and
      a combination of antimicrobials throughout the entire culture medium, the combination comprising a cephalosporinase inhibitor and a third-generation cephalosporin; and
   simultaneously detecting and distinguishing between any ESBL *E. coli* bacteria and ESBL KESC bacteria that are present on the culture medium.

2. The method of claim 1, wherein the third-generation cephalosporin is cefpodoxime.

3. The method of claim 2, wherein the cefpodoxime is present throughout the entire culture medium at a concentration of 0.1 to 32 mg/l.

4. The method of claim 1, wherein the second substrate is 6-chloro-3-indolyl-ß-D-glucuronide.

5. The method of claim 1, wherein the third substrate is tryptophan.

6. A method of detecting and distinguishing between any extended-spectrum β-lactamase-producing *E. coli* bacteria (ESBL *E. coli* bacteria) and any extended-spectrum β-lactamase-producing KESC bacteria (ESBL KESC bacteria) that are present on a culture medium, the method comprising:
  inoculating a culture medium with a biological sample, wherein the culture medium comprises:
    a first substrate for detecting beta-galactosidase activity;
    a second substrate for detecting beta-glucosidase activity; and
    a combination of antimicrobials throughout the entire culture medium, the combination comprising a cephalosporinase inhibitor and a third-generation cephalosporin.

7. The method of claim 6, further comprising:
simultaneously detecting and distinguishing between any ESBL *E. coli* bacteria and ESBL KESC bacteria that are present on the culture medium.

\* \* \* \* \*